(12) United States Patent
Ota et al.

(10) Patent No.: US 9,675,314 B2
(45) Date of Patent: Jun. 13, 2017

(54) METHOD OF TESTING WATERPROOF PERFORMANCE OF RADIOLOGICAL IMAGING APPARATUS, AND RADIOLOGICAL IMAGING APPARATUS

(71) Applicant: Konica Minolta, Inc., Chiyoda-ku, Tokyo (JP)

(72) Inventors: Ikuma Ota, Tokyo (JP); Hajime Ishimoto, Hachioji (JP); Yoshihiko Eguchi, Tokorozawa (JP); Atsunori Shikino, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 32 days.

(21) Appl. No.: 14/947,452

(22) Filed: Nov. 20, 2015

(65) Prior Publication Data
US 2016/0143611 A1    May 26, 2016

(30) Foreign Application Priority Data

Nov. 21, 2014 (JP) .................. 2014-236086

(51) Int. Cl.
*H05G 1/64* (2006.01)
*A61B 6/00* (2006.01)
*G01M 3/32* (2006.01)

(52) U.S. Cl.
CPC ............ *A61B 6/586* (2013.01); *A61B 6/4283* (2013.01); *G01M 3/3218* (2013.01); *G01M 3/3236* (2013.01)

(58) Field of Classification Search
CPC ...... G03B 42/04; G03B 42/02; A61B 6/4233; A61B 6/4283; A61B 6/4435; A61B 6/4488; A61B 6/4423; A61B 2562/247
See application file for complete search history.

(56) References Cited

U.S. PATENT DOCUMENTS

2007/0127625 A1* 6/2007 Hornig ................. G01T 1/2018
378/167
2010/0054406 A1* 3/2010 Kitano .................. G01N 23/04
378/62

(Continued)

FOREIGN PATENT DOCUMENTS

JP        2009121965 A     6/2009
JP        2010151656 A     7/2010

*Primary Examiner* — Hoon Song
(74) *Attorney, Agent, or Firm* — Cantor Colburn LLP

(57) ABSTRACT

A method of testing waterproof performance of a radiological imaging apparatus including: a sensor panel including a plurality of radiation detecting elements two-dimensionally arranged; a housing containing the sensor panel; and an air pressure measuring unit configured to measure an air pressure in the housing having a vent hole allowing the air to flow into and out of the housing, includes: a load application step of continuing to apply a load to the housing; an air pressure measurement step of measuring the air pressure in the housing with the air pressure measuring unit, the air pressure changing while the load is being applied to the housing; and a waterproof performance determination step of determining whether the waterproof performance of the radiological imaging apparatus is normal based on a pattern of change in the measured air pressure in the housing.

18 Claims, 11 Drawing Sheets

(56) References Cited

U.S. PATENT DOCUMENTS

| | | | |
|---|---|---|---|
| 2010/0054416 A1* | 3/2010 | Tsubota | A61B 6/00 378/98 |
| 2011/0222663 A1* | 9/2011 | Utsunomiya | A61B 6/4283 378/98.8 |
| 2012/0076274 A1* | 3/2012 | Shimizukawa | A61B 6/4233 378/98.5 |

* cited by examiner

METHOD OF TESTING WATERPROOF PERFORMANCE OF RADIOLOGICAL IMAGING APPARATUS, AND RADIOLOGICAL IMAGING APPARATUS

CROSS REFERENCE TO RELATED APPLICATIONS

The present invention claims priority under 35 U.S.C. §119 to Japanese Application No. 2014-236086 filed on Nov. 21, 2014, the entire content of which is incorporated herein by reference.

BACKGROUND OF THE INVENTION

Field of the Invention

The present invention relates to a method of testing waterproof performance of a radiological imaging apparatus, and a radiological imaging apparatus. More particularly, the present invention relates to a method of testing waterproof performance of a radiological imaging apparatus that includes radiation detecting elements two-dimensionally arranged.

Description of the Related Art

There are various kinds of radiological imaging apparatuses that have been developed to generate charges at detecting elements in accordance with the dosage of emitted radiation such as X-rays, and read out the generated charges as image data. Radiological imaging apparatuses of this type are known as FPDs (Flat Panel Detectors), and have been conventionally designed as special-purpose apparatuses (also referred to as anchored apparatuses) integrally formed with supporting bases or the like. In recent years, radiological imaging apparatuses of a portable type (also called a cassette type or the like) that have detecting elements and the like housed in housings and can be carried around have been developed and already been put into practical use.

Like a CR (Computed Radiography) cassette conventionally used in radiological imaging, such a portable radiological imaging apparatus has features special-purpose radiological imaging apparatuses do not have. For example, such a portable radiological imaging apparatus can be mounted on a bucky apparatus (see FIG. 4, which will be described later) or be applied directly to the body of a patient, or a patient can be placed on the radiological imaging apparatus during an imaging operation.

However, when a radiological imaging apparatus is applied to the body of a patient, or a patient is placed on a radiological imaging apparatus as described above, urine or blood of the patient might adhere to the radiological imaging apparatus. If the urine or blood adhering to the radiological imaging apparatus penetrates into the housing of the apparatus, the sensor panel (denoted by SP in FIG. 2, which will be described later) having electronic components and the like placed therein might be short-circuited due to the urine or the like penetrating into the housing, or some components might be broken or deteriorate, for example.

Therefore, when the radiological imaging apparatus is subjected to routine maintenance or everyday inspections, for example, a check needs to be made to determine whether the radiological imaging apparatus maintains waterproof performance. As a method for such a check, JP 2009-121965 A discloses a waterproof performance testing method. According to JP 2009-121965 A, an air pressure sensor is included in the housing of an apparatus, and the apparatus is placed in a testing device. The air pressure in the apparatus is measured as the atmospheric pressure outside the apparatus is changed. A check is then made to determine whether the waterproof performance of the apparatus is normal based on whether the measured air pressure in the apparatus is equal to or lower than a predetermined amount of air pressure change.

JP 2010-151656 A also discloses a waterproof performance testing method. According to JP 2010-151656 A, the housing of an apparatus contains an air pressure sensor, a temperature sensor, and a temperature changing unit that changes the temperature in the housing. The change in the air pressure with respect to the temperature before and after the temperature in the housing is changed by the temperature changing unit is measured with the air pressure sensor. The result of the determination is compared with a theoretical value calculated in a case where the housing is completely sealed, and the waterproof performance of the apparatus is then determined.

However, in a case where the waterproof performance testing method disclosed in JP 2009-121965 A is applied in testing the waterproof performance of a radiological imaging apparatus, there is the need to not only prepare a testing device equipped with a chamber or the like that can change the inner air pressure, or but also take the testing device to a place where the radiological imaging apparatus exists or take the radiological imaging apparatus to a place where the testing device exists. Therefore, the waterproof performance of the radiological imaging apparatus is not readily tested.

In a case where the waterproof performance testing method disclosed in JP 2010-151656 A is applied in testing the waterproof performance of a radiological imaging apparatus, it is necessary to prepare not only an air pressure sensor but also a temperature sensor and a temperature changing unit that changes the temperature in the housing. Furthermore, after the temperature in the housing is changed by the temperature changing unit, a long period of time is required until the temperature stabilizes, and an even longer period of time is required to test the waterproof performance of the radiological imaging apparatus.

SUMMARY OF THE INVENTION

The present invention has been made in view of the above problems, and an object thereof is to provide a method of testing waterproof performance of a radiological imaging apparatus for accurately testing waterproof performance of the radiological imaging apparatus, and readily conducting the testing in a relatively short period of time, and a radiological imaging apparatus.

To achieve the abovementioned object, according to an aspect, a method of testing waterproof performance of a radiological imaging apparatus, the radiological imaging apparatus including: a sensor panel including radiation detecting elements two-dimensionally arranged; a housing containing the sensor panel; and an air pressure measuring unit that measures the air pressure in the housing, the housing having a vent hole allowing the air to flow into and out of the housing, the method reflecting one aspect of the present invention comprises: a load application step of continuing to apply a load to the housing of the radiological imaging apparatus; an air pressure measurement step of measuring the air pressure in the housing with the air pressure measuring unit, the air pressure changing while the load is being applied to the housing of the radiological imaging apparatus; and a waterproof performance determination step of determining whether the waterproof performance of the radiological imaging apparatus is normal based on a pattern of change in the measured air pressure in the housing.

To achieve the abovementioned object, according to an aspect, a method of testing waterproof performance of a radiological imaging apparatus, the radiological imaging apparatus also including: a sensor panel including radiation detecting elements two-dimensionally arranged; a housing containing the sensor panel; and an air pressure measuring unit that measures the air pressure in the housing, the housing having a vent hole allowing the air to flow into and out of the housing, the method reflecting one aspect of the present invention comprises: a load application step of applying a load to the housing of the radiological imaging apparatus to release the air in the housing to the outside through the vent hole; an air pressure measurement step of measuring the air pressure in the housing with the air pressure measuring unit, the air pressure continuing to increase after the application of the load is stopped; and a waterproof performance determination step of determining whether the waterproof performance of the radiological imaging apparatus is normal based on a pattern of change in the measured air pressure in the housing.

To achieve the abovementioned object, according to an aspect, a method of testing waterproof performance of a radiological imaging apparatus, the radiological imaging apparatus including: a sensor panel including radiation detecting elements two-dimensionally arranged; a housing containing the sensor panel; a speaker that is provided in the housing and emits sound; and a microphone that is provided in the housing and converts the sound into audio data, the method reflecting one aspect of the present invention comprises: a recording step of converting the sound emitted from the speaker in the housing into the audio data and recording the audio data; a frequency analysis step of subjecting the recorded audio data to frequency analysis; and a waterproof performance determination step of determining whether the waterproof performance of the radiological imaging apparatus is normal based on a distribution of the intensity of the audio data subjected to the frequency analysis with respect to frequency.

To achieve the abovementioned object, according to an aspect, a radiological imaging apparatus reflecting one aspect of the present invention comprises: a sensor panel including radiation detecting elements two-dimensionally arranged; a housing containing the sensor panel; a speaker that is provided in the housing and emits sound; a microphone that is provided in the housing, and converts the sound into audio data and records the audio data, an analyzing unit that subjects the audio data to frequency analysis, the audio data being converted from the sound emitted from the speaker in the housing and being recorded with the microphone; and a determining unit that determines whether the waterproof performance of the radiological imaging apparatus is normal based on a distribution of the intensity of the audio data subjected to the frequency analysis with respect to frequency.

BRIEF DESCRIPTION OF THE DRAWINGS

The above and other objects, advantages and features of the present invention will become more fully understood from the detailed description given hereinbelow and the appended drawings which are given byway of illustration only, and thus are not intended as a definition of the limits of the present invention, and wherein.

DESCRIPTION OF THE PREFERRED EMBODIMENTS

Hereinafter, embodiments of a method of testing waterproof performance of a radiological imaging apparatus and a radiological imaging apparatus according to the present invention will be described with reference to the drawings. However, the scope of the invention is not limited to the illustrated examples.

In the description below, a radiological imaging apparatus of a so-called indirect type that includes a scintillator and the like, and obtains image data with radiation detecting elements converting emitted radiation into electromagnetic waves of another wavelength such as visible light will be described as a radiological imaging apparatus. However, the present invention can also be applied to a radiological imaging apparatus of a so-called direct type that detects radiation with radiation detecting elements without a scintillator or the like.

[Structure and the Like of a Radiological Imaging Apparatus]

Figure 1:
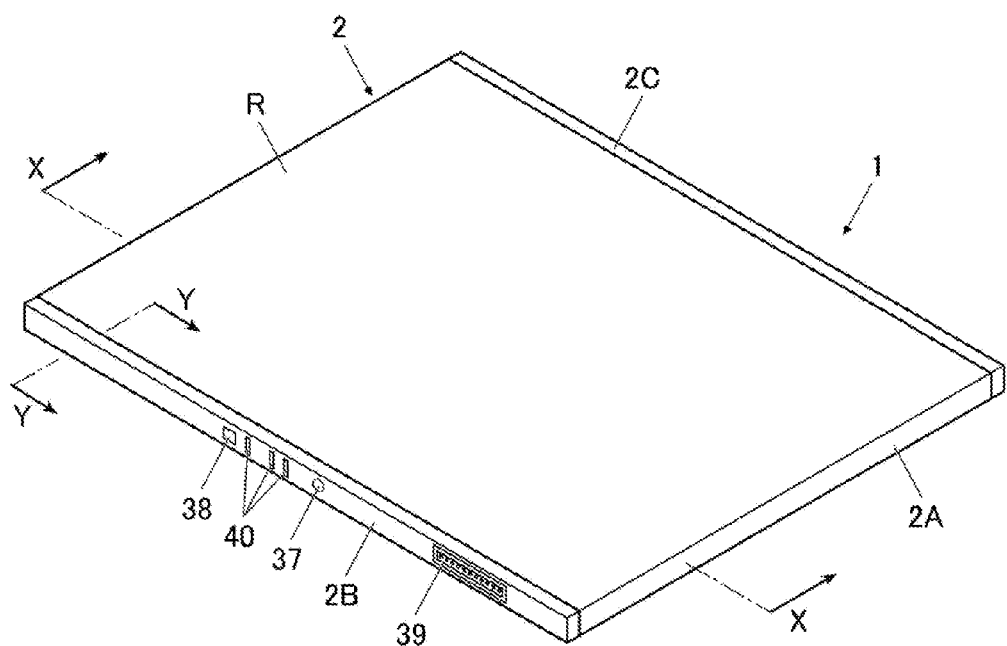
FIG. 1 is a perspective view of the exterior of a radiological imaging apparatus according to this embodiment.
Figure 2:
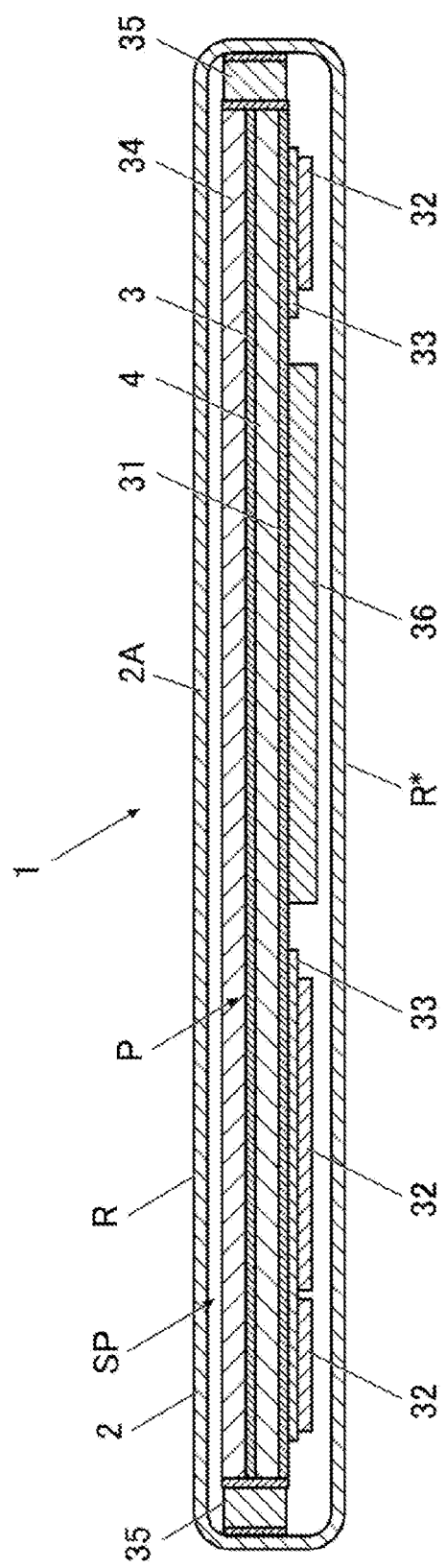
FIG. 2 is a cross-sectional view of the radiological imaging apparatus, taken along the line X-X defined in FIG. 1.

Before a method of testing waterproof performance of a radiological imaging apparatus according to this embodiment is explained, the basic structure and the like of a radiological imaging apparatus is briefly described. FIG. 1 is a perspective view of the exterior of a radiological imaging apparatus. FIG. 2 is a cross-sectional view of the radiological imaging apparatus, taken along the line X-X defined in FIG. 1. In the description below, the vertical direction in FIG. 2 will be described as the vertical direction in the radiological imaging apparatus 1, for ease of explanation.

As shown in FIG. 1, the radiological imaging apparatus 1 is formed by placing a sensor panel SP formed with a scintillator 3, a sensor substrate 4, and the like in a housing 2 having a radiation incidence surface R that is the surface on the side to which radiation is to be emitted. In FIG. 2, R* represents the surface of the housing 2 on the opposite side from the radiation incidence surface R. Hereinafter, this surface R* will be referred to as the bottom surface R*.

As shown in FIGS. 1 and 2, in this embodiment, the housing main frame 2A that is a hollow rectangular cylinder having the radiation incidence surface R of the housing 2 is formed with a radiotransparent carbon plate (or carbon fiber solidified in a plate-like form with resin), and the housing 2 is formed by closing the openings at both sides of the housing main frame 2A with protective covers 2B and 2C.

Instead of being formed by closing the openings at both sides of the rectangular-cylindrical housing main frame 2A with the protective covers 2B and 2C as described above, the housing 2 of the radiological imaging apparatus 1 may be a housing having a lunchbox-like shape, for example, though not shown in the figure. That is, the housing 2 may be a housing that houses the sensor panel SP in such a manner as to cover the sensor panel SP from above and below when the sensor panel SP is placed so that the planar direction thereof becomes the horizontal direction as shown in FIG. 2, for example.

In this embodiment, the protective covers 2B and 2C are provided with antennas (not shown) for conducting wireless communication with an external device. The protective cover 2B on one side of the housing 2 is provided with a power switch 37, a selector switch 38, a connector 39, and indicators 40 formed with LEDs (Light Emitting Diodes) or the like that display a battery state, an operating state of the apparatus, or the like.

As shown in FIG. 2, a base 31 is placed in the housing 2, and the sensor substrate 4 is placed above the base 31 (or on the side of the radiation incidence surface R) via a lead thin plate (not shown) or the like. The scintillator 3 that converts emitted radiation into light such as visible light, and a scintillator substrate 34 that supports the scintillator 3 are provided on the upper surface side of the sensor substrate 4.

Figure 3:
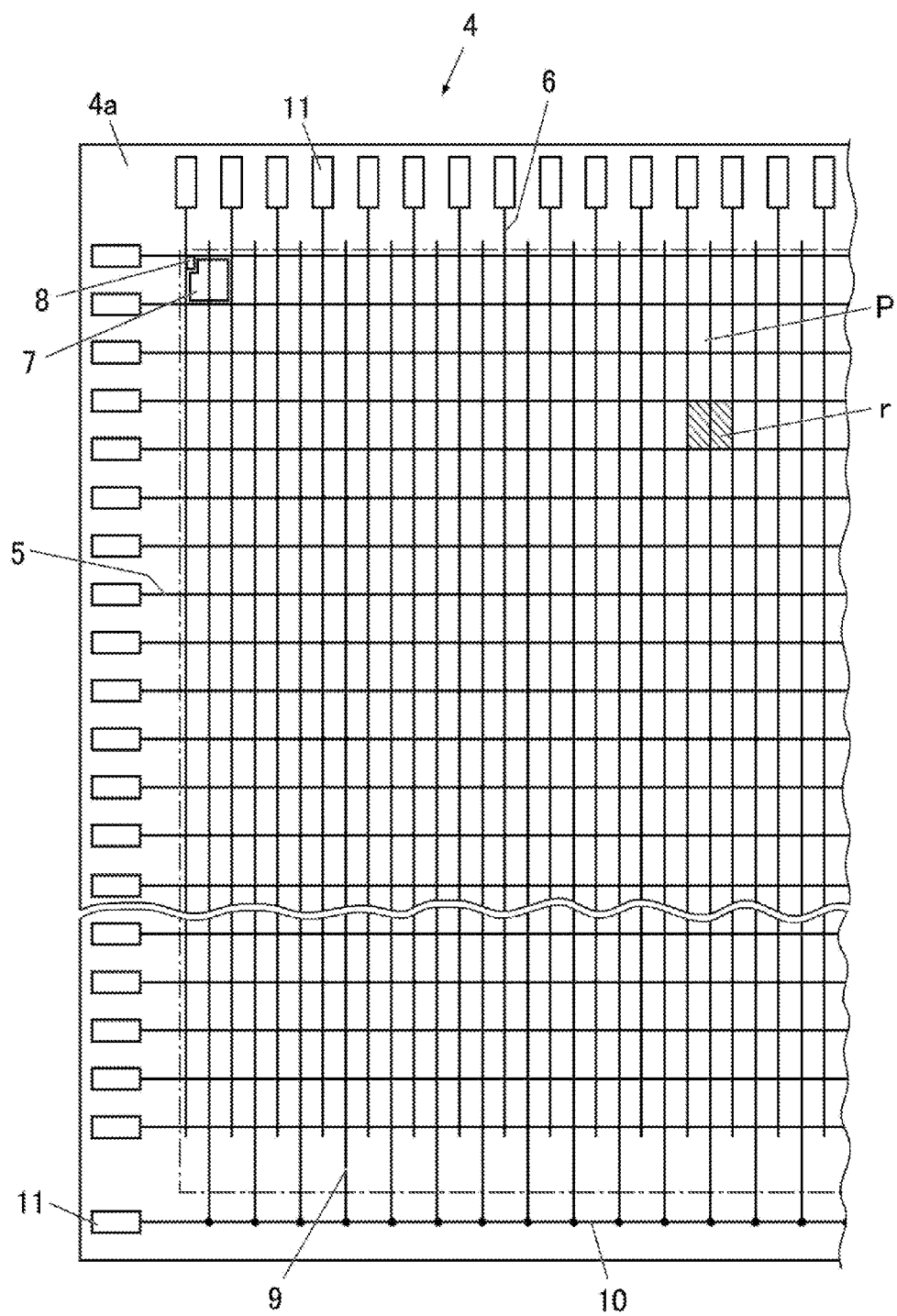
FIG. 3 is a plan view showing the structure of a sensor substrate of the radiological imaging apparatus.

In this embodiment, the sensor substrate 4 is formed with a glass substrate, and scanning lines 5 and signal lines 6 are arranged so as to intersect each other on the upper surface (or the surface facing the scintillator 3) 4a of the sensor substrate 4 as shown in FIG. 3. Further, a radiation detecting element 7 is provided in each of the small regions r defined by the scanning lines 5 and the signal lines 6 on the surface 4a of the sensor substrate 4.

In this embodiment, the region in which the radiation detecting elements 7 are arranged in a two-dimensional pattern (a matrix fashion), or the region indicated by a dot-and-dash line in FIG. 3, is the detecting unit P. Further, in this embodiment, the radiation detecting elements 7 are photodiodes, but it is possible to use phototransistors or the like, for example.

PCB substrates 33 having electronic components 32 and the like provided thereon, a battery 36, and the like are attached to the lower surface of the base 31. The scanning lines 5, the signal lines 6, and the like arranged on the surface 4a of the sensor substrate 4 are extended to the lower surface side of the base 31 via input/output terminals 11 (see FIG. 3) and a flexible circuit board (also called a chip-on-film or the like) (not shown) or the like, and are thus connected to the various kinds of electronic components 32.

As shown in FIG. 3, bias lines 9 are connected to the respective radiation detecting elements 7, and each of the bias lines 9 is connected to a connecting wire 10 in a peripheral region of the upper surface 4a of the sensor substrate 4. The connecting wire 10 is connected to a bias supply (not shown) on the lower surface side of the base 31 via the input/output terminals 11 and the flexible circuit board (not shown) or the like. Accordingly, a so-called reverse bias voltage supplied from the bias supply is applied to the respective radiation detecting elements 7 via the connecting wire 10 and the bias lines 9.

In this embodiment, the sensor panel SP (see FIG. 2) of the radiological imaging apparatus 1 is formed in the above manner. In this embodiment, a buffer material 35 is provided between the sensor panel SP and the inner side surfaces of the housing 2.

When the radiological imaging apparatus 1 is transported by air or is used in a place at a high altitude, for example, the air pressure in the housing 2 of the radiological imaging apparatus 1 might become higher than the outside atmospheric pressure, and the housing 2 might be expanded, resulting in damage or the like in the sensor panel SP. So as to prevent that, vent holes for allowing the air to flow into and out of the housing 2 are formed in the housing 2 of the radiological imaging apparatus 1.

Figure 4:
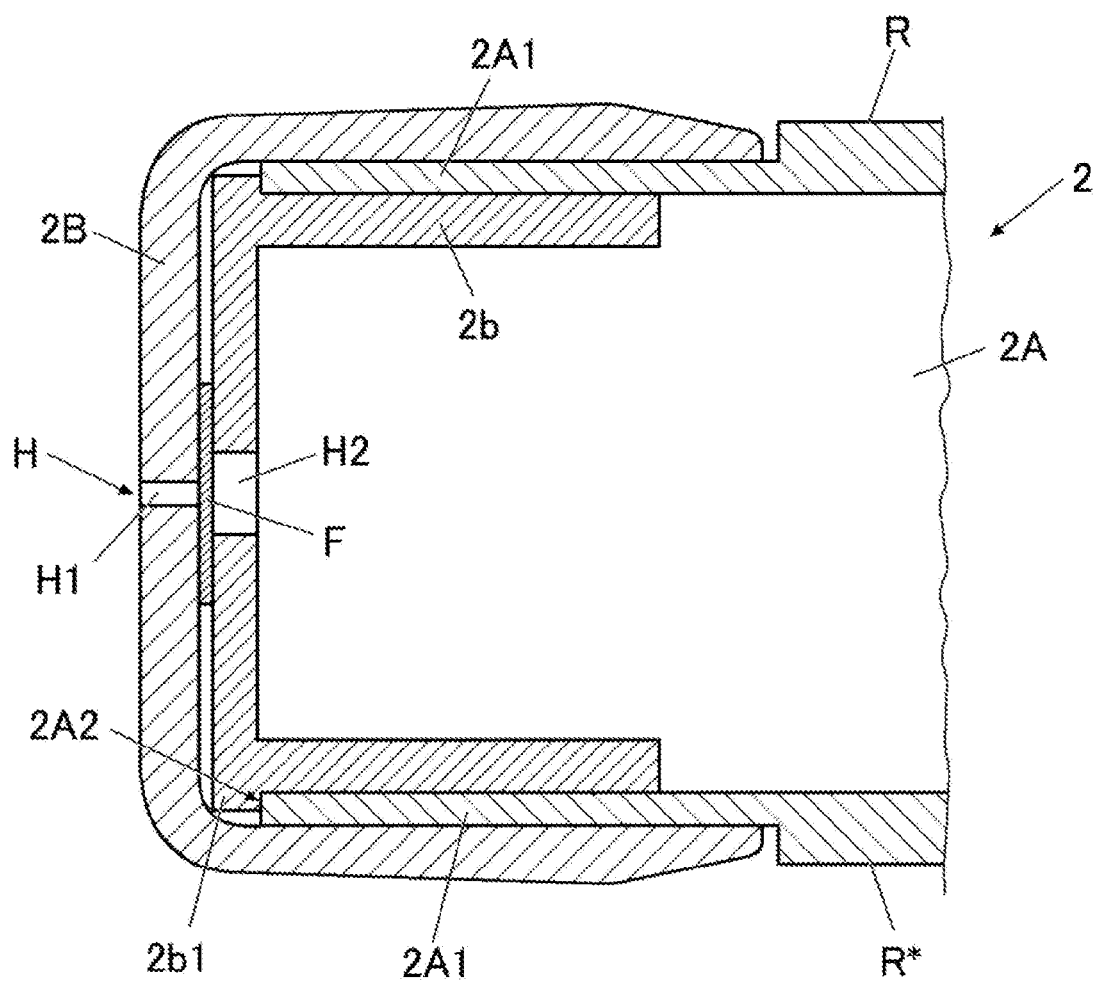
FIG. 4 is a cross-sectional view of the radiological imaging apparatus, taken along the Y-Y line defined in FIG. 1.

The vent holes can be formed at portions of the bottom surface R* of the housing main frame 2A (see FIG. 2 and others) of the housing 2, peripheral portions of the radiation incidence surface R, or side surfaces of the housing main frame 2A, for example. In this embodiment, the vent holes are formed in the side surface portions of the housing 2 at which the protective covers 2B and 2C are provided. FIG. 4 is a cross-sectional view of the radiological imaging apparatus 1, taken along the Y-Y line defined in FIG. 1.

In this embodiment, an inner cover 2b is inserted inside the end portions 2A1 of the housing main frame 2A of the housing 2, and locking parts 2b1 of the inner cover 2b engage with the edge portions 2A2 of the end portions 2A1, so that the opening of the housing main frame 2A is sealed with the inner cover 2b. In this state, the protective cover 2B is attached to the housing main frame 2A in such a manner so as to cover those components from outside, and the opening of the housing main frame 2A is closed. The side of the protective cover 2C is the same.

In this embodiment, holes H1 and H2 are drilled in the protective cover 2B and the inner cover 2b, and are arranged to continue to each other, so that a vent hole H is formed in the side surface of the housing 2 of the radiological imaging apparatus 1. Since a fluid such as urine of a patient would penetrate into the housing 2 through the vent hole H, a ventilation filter F is provided in the vent hole H so as to prevent penetration of a fluid into the housing 2 but allow air ventilation.

With this structure, the air inside and the outside the housing 2 flows through the vent hole H formed with the holes H1 and H2 formed in the protective cover 2B and the inner cover 2b, respectively, and also flows through the ventilation filter F. The ventilation filter F can be a film made of a fluororesin-based material, such as a PTFE (polytetrafluoroethylene) porous film. However, it is possible to use a film or the like that has ventilation characteristics and is made of a material other than the above, as long as it has the above described function. The shape of the vent hole H is not limited to the above, and may have any shape, as long as the vent hole H can allow the air to flow into and out of the housing 2.

[Methods of Testing Waterproof Performance of the Radiological Imaging Apparatus]

Next, waterproof performance testing methods to be conducted on the radiological imaging apparatus 1 having the above structure will be described. In the description below, the waterproof performance testing methods will be described through several embodiments. The methods of testing waterproof performance of the radiological imaging apparatus 1 will also be described in conjunction with the effects of the radiological imaging apparatus 1.

First Embodiment

A first embodiment concerns a case where an air pressure measuring unit such as an air pressure sensor that measures the air pressure inside the housing 2 is provided in the housing 2, and a check is made to determine whether the waterproof performance of the radiological imaging apparatus 1 is normal based on the air pressure inside the housing 2 measured by the air pressure measuring unit, as by the waterproof performance testing method disclosed in JP 2009-121965 A.

By the waterproof performance testing method disclosed in JP 2009-121965 A, a testing device for changing the atmospheric pressure outside the apparatus is required. In this embodiment, however, such a testing device is unnecessary. Further, by the waterproof performance testing method disclosed in JP 2009-121965 A, the atmospheric pressure outside the apparatus is changed. In this embodiment, however, the atmospheric pressure outside the housing 2 of the radiological imaging apparatus 1 is not changed, as will be described below.

Figure 5A:
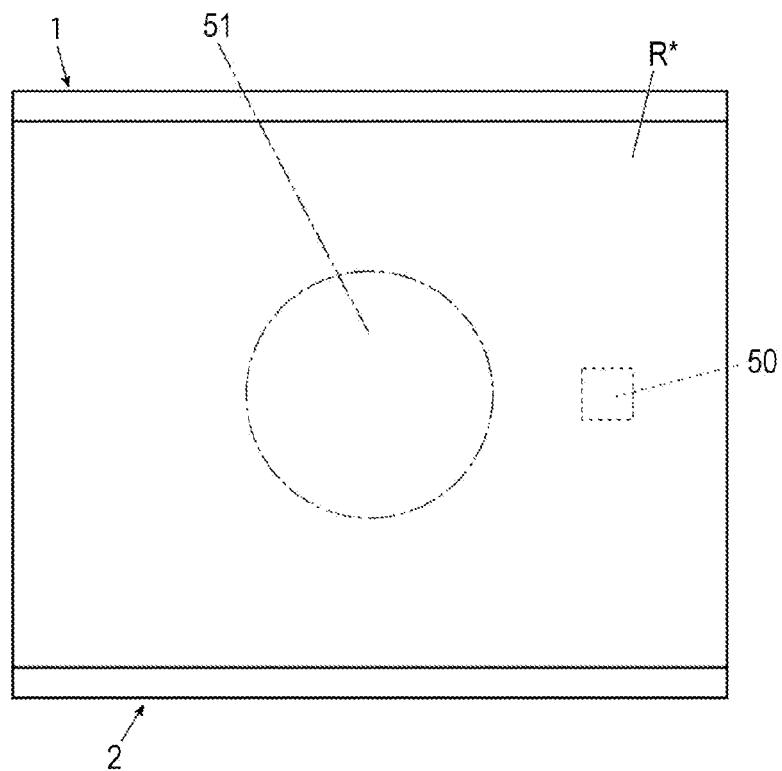
FIG. 5A is a diagram showing the structure of each radiological imaging apparatus according to first to third embodiments.

As shown in FIG. 5A, in this embodiment, an air pressure measuring unit 50 formed with an air pressure sensor or the like that measures the air pressure inside the housing 2 is provided in a PCB substrate 33 (see FIG. 2) placed on the lower surface side of the base 31, for example, inside the housing 2 of the radiological imaging apparatus 1. The air pressure measuring unit 50 is designed to transmit the data of the measured air pressure to the control unit (not shown) of the radiological imaging apparatus 1 formed with a CPU (Central Processing Unit) or an FPGA (Field Programmable Gate Array). The portion denoted by reference numeral 51 in FIG. 5A will be described later.

In the example case described below, the control unit of the radiological imaging apparatus 1 carries out a waterproof performance testing process on the radiological imaging apparatus 1. However, necessary information such as air pressure data may be transferred from the radiological imaging apparatus 1 to an external computer such as a console, and the external computer may carry out a waterproof performance testing process on the radiological imaging apparatus 1. In this aspect, the second embodiment and each of the embodiments described below are the same as the first embodiment.

Figure 5B:
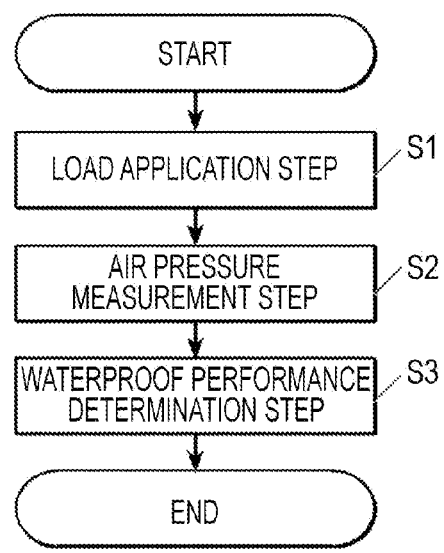
FIG. 5B is a flowchart showing the respective steps in each method of testing waterproof performance of a radiological imaging apparatus according to the first to third embodiments.

As shown in the flowchart in FIG. 5B, a method of testing waterproof performance of a radiological imaging apparatus according to this embodiment basically includes the three steps: a load application step (step S1), an air pressure measurement step (step S2), and a waterproof performance determination step (step S3).

In the load application step (step S1), a certain load continues to be applied to the housing 2 of the radiological imaging apparatus 1. At this point, the load is applied as a user or maintenance personnel may continue to press the bottom surface R* (see FIG. 2 and others) of the radiological imaging apparatus 1 placed upside down with a certain amount of force with a hand, or place a predetermined weight or the like on the bottom surface R* of the radiological imaging apparatus 1.

If the housing 2 of the radiological imaging apparatus 1 is soft, the radiation incidence surface R (see FIGS. 1 and 2) of the radiological imaging apparatus 1 is bent when the body of a patient is placed on the radiation incidence surface R, and the bent radiation incidence surface R presses the scintillator substrate 34. As a result, the columnar crystal of the fluorescent material of the scintillator 3 might be damaged between the scintillator substrate 34 and the sensor substrate 4. Therefore, the housing 2 of the radiological imaging apparatus 1 is often made of a secure material such as a carbon plate, as in this embodiment. Accordingly, even if the bottom surface R* of the radiological imaging apparatus 1 is pressed with a hand as described above, for example, the bottom surface R* is unlikely to be easily deformed.

In view of this, as shown in FIG. 5A, for example, a portion 51 of the bottom surface R* or the like of the radiological imaging apparatus 1 is formed with a material that is softer than the other portions of the housing 2 but has a certain degree of strength, and a user or maintenance personnel can apply a load to the portion 51 by pressing the portion 51 with a hand or placing a weight on the portion 51.

In this structure, the portion 51 can be deformed by a smaller load, and the air pressures P inside the housing 2 can be changed more readily than in a case where a load is applied to the bottom surface R* or the like of the radiological imaging apparatus 1 without the above described portion 51. Accordingly, the force to be applied to the portion 51 and the weight to be put on the portion 51 can be readily adjusted, and the accuracy in determination of the waterproof performance of the radiological imaging apparatus 1 can be further increased. The portion 51 that is softer than the other portions of the housing 2 is formed in at least one part of the housing 2, and almost the entire bottom surface R* of the radiological imaging apparatus 1 or some part of the radiation incidence surface R of the radiological imaging apparatus 1 may be soft, for example.

Figure 6A:
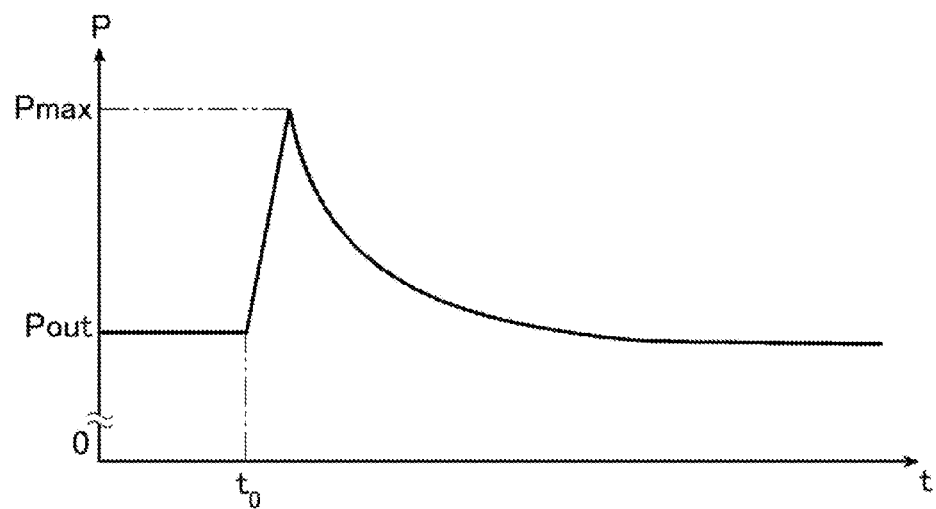
FIG. 6A is a graph showing an example of the time-series data of the air pressure in the housing measured in an air pressure measurement step in the first and second embodiments.

In the air pressure measurement step (step S2), the air pressure in the housing 2 that changes while a load continues to be applied to the housing 2 of the radiological imaging apparatus 1 as described above is measured by the air pressure measuring unit 50, and the time-series data of the air pressure P in the housing 2 shown in FIG. 6A is obtained, for example.

In this case, the air pressure P inside the housing 2 fluctuates over time as shown in FIG. 6A, for example.

Specifically, at the time when the application of a load to the housing 2 of the radiological imaging apparatus 1 is started (time $t_0$), the air pressure P inside the housing 2 shoots up and reaches the maximum value Pmax of the air pressure P. The air inside the housing 2 then flows out through the vent hole H (see FIG. 4) and the ventilation filter F, and the air pressure P inside the housing 2 gradually drops. If the application of the same load is continued, the air pressure P eventually drops to the same air pressure as the air pressure prior to the application of the load (this air pressure is the same as the outside atmospheric pressure, and therefore, will be hereinafter referred to as the outside atmospheric pressure Pout).

In the waterproof performance determination step (step S3), a check is made to determine whether the waterproof performance of the radiological imaging apparatus 1 is normal based on the pattern of change in the air pressure P measured inside the housing 2.

Although not shown in FIGS. 1 and 4, for example, if the sealing between the end portions 2A1 of the housing main frame 2A of the housing 2 and the inner cover 2b (see FIG. 4) provided inside the end portions 2A1, or the shields or packings or the like provided at the power switch 37, the selector switch 38, the connector 39, the indicators 40, and the like (see FIG. 1) are damaged or deteriorate over time, moisture penetrates into the housing 2 through such damaged portions.

If the housing main frame 2A or the protective covers 2B and 2C (see FIGS. 1 and 2) of the housing 2 are damaged as the radiological imaging apparatus 1 is dropped, for example, moisture might penetrate into the housing 2 through the damaged portions. In this manner, the waterproof performance of the radiological imaging apparatus 1 deteriorates. As the waterproof performance of the radiological imaging apparatus 1 deteriorates, the air flows into the housing 2 through the above mentioned damaged portions or flows out of the housing 2 through the damaged portions.

In a case where the above described method of testing waterproof performance of a radiological imaging apparatus is implemented for the radiological imaging apparatus 1 in a normal state without any waterproof performance deterioration at the time of shipment from the factory, and the load application step (step S1) and the air pressure measurement step (step S2) are carried out at the time, for example, the air in the housing 2 flows out only through the ventilating portions such as the vent hole H (see FIG. 4) having the ventilation filter F.

Figure 6B:
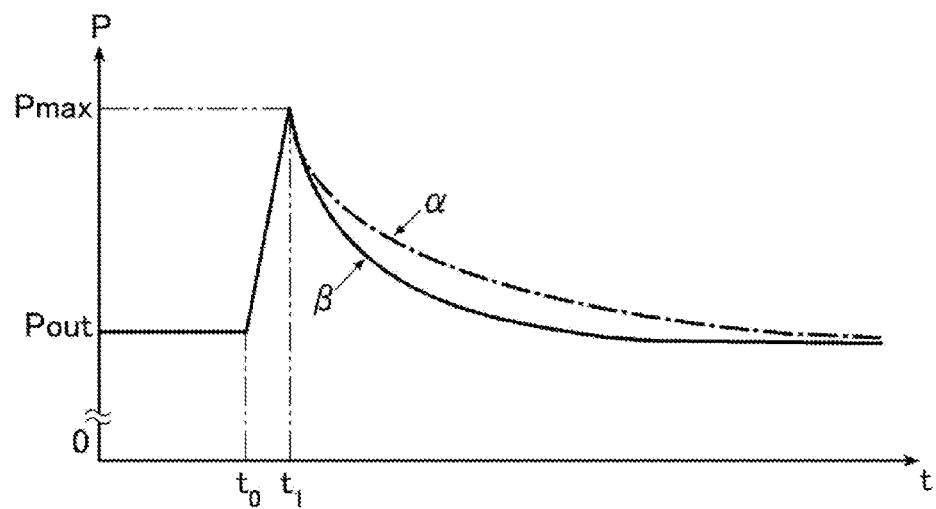
FIG. 6B is a graph showing an example of the time-series data of the air pressure in a case where the waterproof performance has deteriorated, and an example of the time-series data of the air pressure in a case where the waterproof performance has not deteriorated.

Therefore, as indicated by a dot-and-dash line α in the graph in FIG. 6B, for example, in the radiological imaging apparatus 1 in a normal state without any waterproof performance deterioration, the air pressure P inside the housing 2 shoots up from the outside atmospheric pressure Pout when a certain load is applied (time $t_0$), and reaches the maximum value Pmax of the air pressure P. After that, the air pressure P inside the housing 2 gradually drops.

If the air flows into the housing 2 or flows out of the housing 2 through portions other than the vent hole H having the ventilation filter F as the waterproof performance deteriorates and the shields and packings are damaged as described above, the air pressure P inside the housing 2 shoots up from the outside atmospheric pressure Pout when a certain load is applied (time $t_0$), but the decrease rate of the air pressure P inside the housing 2 after the air pressure P inside the housing 2 reaches the maximum value Pmax of the air pressure P is high, as indicated by a solid line β in the graph in FIG. 6B, for example.

In view of this, in the waterproof performance determination step (step S3 in FIG. 5B) of this embodiment, the temporal change in the air pressure P inside the housing 2 at the time of the load application in the radiological imaging apparatus 1 in the brand-new state without any waterproof performance deterioration such as the time of the shipment from the factory or the like (see α in FIG. 6B) is compared with the temporal change in the air pressure P inside the housing 2 at the time of the load application in the radiological imaging apparatus 1 after the start of usage (see β in FIG. 6B). In this manner, a check is made to determine whether the waterproof performance of the radiological imaging apparatus 1 is normal, and determine a degree of deterioration.

This aspect is described below in detail. The temporal change in the air pressure P inside the housing 2 at the time of the load application in the radiological imaging apparatus 1 in the brand-new state without any waterproof performance deterioration (see α in FIG. 6B) is measured (or may be theoretically calculated) beforehand through an experiment in which the load to be applied to the housing 2 of the radiological imaging apparatus 1 is varied. In this manner, the necessary information described below such as a change rate and time is calculated beforehand with respect to each load applied to the housing 2 of the radiological imaging apparatus 1. These pieces of information are then stored into the memory of the control unit of the radiological imaging apparatus 1, or are written into a program.

In the above described waterproof performance determination step, a check can be made to determine whether the waterproof performance of the radiological imaging apparatus 1 is normal and determine a degree of deterioration based on the change rate of the measured air pressure P in the housing 2 (see the first determination technique described below), the time T that has passed before the air pressure P inside the housing 2 drops to a predetermined air pressure (see the second determination technique described below), or the amount of change ΔP in the air pressure P that has dropped in a predetermined time Δt (see the third determination technique described below). The first to third determination techniques described below are examples of determination techniques that can be used in the waterproof performance determination step (step S3). However, a determination technique in the waterproof performance determination step in a method of testing waterproof performance of a radiological imaging apparatus according to the present invention is to determine whether the waterproof performance of the radiological imaging apparatus 1 is normal based on the pattern of change in the air pressure P measured in the housing 2, and is not limited to the first to third determination techniques described below.

[First Determination Technique]

In a case where the waterproof performance of the radiological imaging apparatus 1 is determined based on a change rate of the measured air pressure P in the housing 2 as described above, the load application step (step S1) and the air pressure measurement step (step S2) are carried out, to measure the air pressure P inside the housing 2 of the radiological imaging apparatus 1 with the air pressure measuring unit 50, and obtain time-series data of the air pressure P in the housing 2 as indicated by the solid line β in FIG. 6B, for example.

In the waterproof performance determination step (step S3 in FIG. 5B), the change rate (also called the decrease rate) of the air pressure P in the housing 2 after the air pressure P in the housing 2 measured by the air pressure measuring unit 50 increases to the maximum value Pmax is calculated, and the change rate corresponding to the difference Pmax-Pout between the maximum value Pmax of the air pressure P in the housing 2 measured by the air pressure measuring unit 50 this time and the outside atmospheric pressure Pout is read from among the change rates calculated beforehand and written in a memory or a program in the radiological imaging apparatus 1 in the brand-new state. The calculated change rate is compared with the read change rate, to determine whether the waterproof performance of the radiological imaging apparatus 1 is normal, and determine the degree of deterioration.

In a case where the change rate corresponding to the difference Pmax-Pout between the maximum value Pmax of the air pressure P in the housing 2 measured by the air pressure measuring unit 50 this time and the outside atmospheric pressure Pout is not found in the memory or the program, a change rate in the radiological imaging apparatus 1 in the brand-new state in the case of the difference Pmax-Pout between the maximum value Pmax measured this time and the outside atmospheric pressure Pout is calculated based on the change rates corresponding to values close to the difference Pmax-Pout between the maximum value Pmax measured this time and the outside atmospheric pressure Pout, and it can be calculated with the calculated change rate.

Alternatively, the above described change rate may be the time derivative dP/dt of the air pressure P in the housing 2 (or $\Delta P/\Delta t$ calculated from a predetermined time interval $\Delta t$ and the amount of change $\Delta P$ in the air pressure P during the time interval $\Delta t$; the same applies in the cases described below). In a case where the time derivative dP/dt depends on the difference Pmax-Pout between the maximum value Pmax of the air pressure P in the housing 2 and the outside atmospheric pressure Pout, it is possible to use a time derivative dP/dt/(Pmax-Pout) per unit air pressure, which is obtained by dividing dP/dt by Pmax-Pout. Alternatively, the amount of change $\Delta P$ in the air pressure P in the predetermined time interval $\Delta t$ (or $\Delta P$ not divided by $\Delta t$) may be used as the above described change rate. The above described change rate is not particularly limited to a specific value, as long as it can express the change in the air pressure P in the housing 2 after the air pressure P in the housing 2 increases to the maximum value Pmax.

The outside atmospheric pressure Pout is calculated as the mean value of the air pressure P in the housing 2 of the radiological imaging apparatus 1 immediately before the start of the load application step (step S1).

The calculated change rate is then compared with the change rate in the radiological imaging apparatus 1 in the brand-new state (or in a state where the waterproof performance is normal). If there is no significant difference between the two change rates, the waterproof performance of the radiological imaging apparatus 1 is determined to be normal. If there is a significant difference between the two change rates, the waterproof performance of the radiological imaging apparatus 1 can be determined not to be normal, or the waterproof performance can be determined to have deteriorated.

Alternatively, a check can be made to determine to what degree the waterproof performance of the radiological imaging apparatus 1 has deteriorated, or determine the degree of deterioration, based on the size of the difference between the two change rates.

[Second Determination Technique]

In a case where the waterproof performance of the radiological imaging apparatus 1 is determined based on the time that has passed before the air pressure P in the housing 2 drops to a predetermined air pressure as described above, the load application step (step S1) and the air pressure measurement step (step S2) are carried out, to measure the air pressure P inside the housing 2 of the radiological imaging apparatus 1 with the air pressure measuring unit 50, and obtain time-series data of the air pressure P in the housing 2 as indicated by the solid line β in FIG. 6B, for example.

Figure 7A:
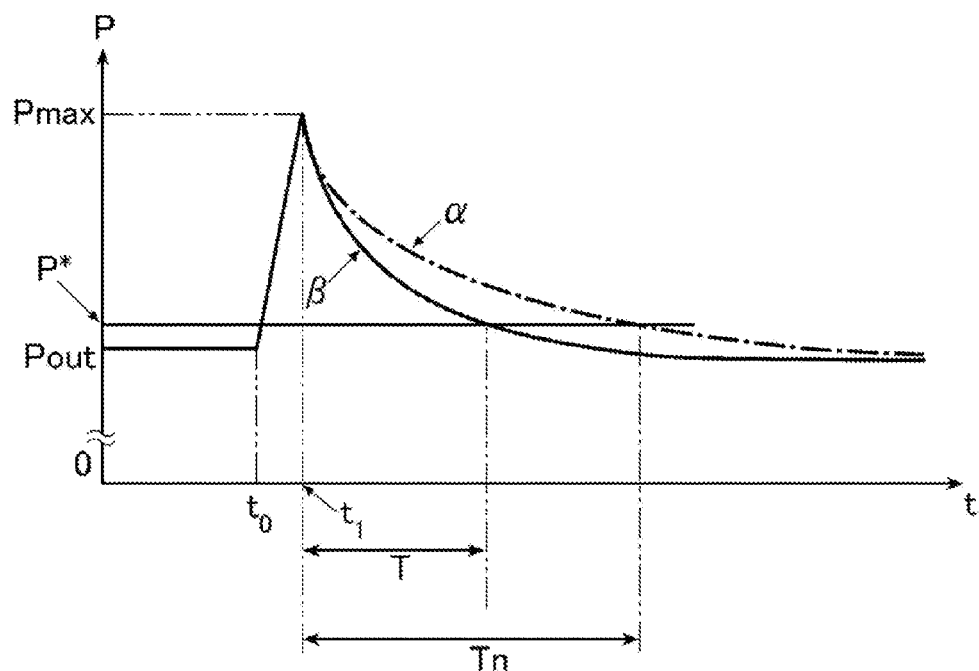
FIG. 7A is a graph for explaining a second determination technique.

In the waterproof performance determination step (step S3 in FIG. 5B), the time T that has passed since the time (time $t_1$) when the air pressure P in the housing 2 measured by the air pressure measuring unit 50 increased to the maximum value Pmax till the air pressure P drops to a predetermined air pressure P* such as 10% of the difference Pmax-Pout between the maximum value Pmax and the outside atmospheric pressure Pout is calculated, for example. To be exact, as shown in FIG. 7A, the time T that has passed since the air pressure P in the housing 2 increased to the maximum value Pmax till the air pressure P drops to an air pressure P* that is higher than the outside atmospheric pressure Pout by (Pmax-Pout)×0.1 is calculated according to $$P^* = P\text{out} + (P\text{max} - P\text{out}) \times 0.1 \tag{1}$$

The predetermined air pressure P* is not limited to the above, and may be set at an appropriate value.

The calculated time T is then compared with a time Tn (see FIG. 7A) in the radiological imaging apparatus 1 in the brand-new state (or in a state where the waterproof performance is normal). If there is no significant difference between the two times T and Tn, the waterproof performance of the radiological imaging apparatus 1 is determined to be normal. If there is a significant difference between the two times T and Tn, the waterproof performance of the radiological imaging apparatus 1 can be determined not to be normal, or the waterproof performance can be determined to have deteriorated.

Alternatively, a check can be made to determine to what degree the waterproof performance of the radiological imaging apparatus 1 has deteriorated, or determine the degree of deterioration, based on the size of the difference between the two times T and Tn.

[Third Determination Technique]

Further, it is possible to determine whether the waterproof performance of the radiological imaging apparatus 1 is normal or determine the degree of deterioration based on the amount of change $\Delta P$ in the air pressure P that has decreased in a predetermined time $\Delta t$, as described above.

Figure 7B:
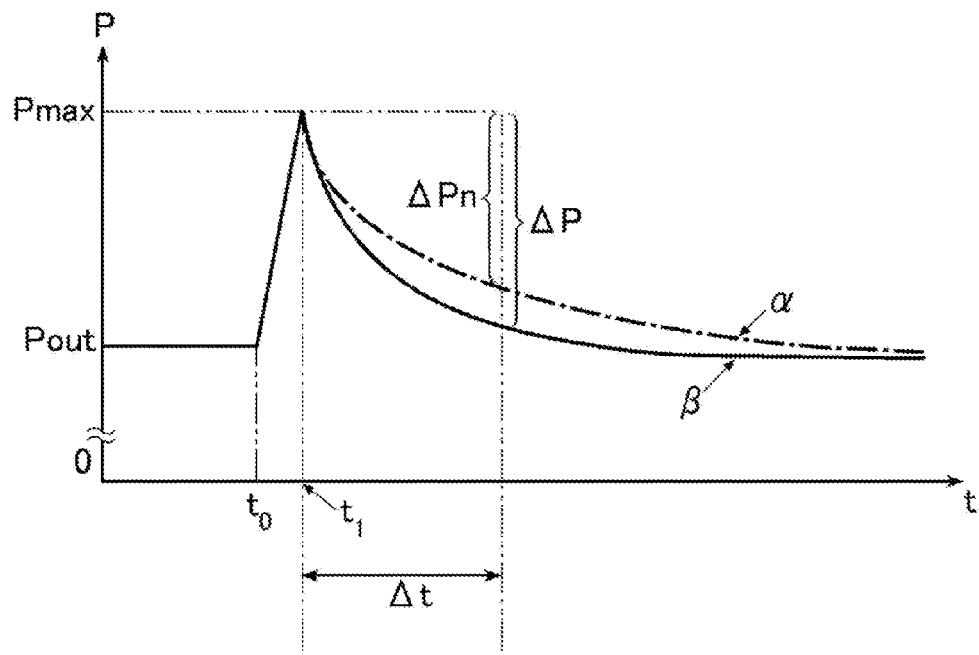
FIG. 7B is a graph for explaining a third determination technique.

In the waterproof performance determination step (step S3 in FIG. 5B) in this case, as shown in FIG. 7B, for example, the amount of change $\Delta P$ in the air pressure P that has dropped in the predetermined time $\Delta t$ after the time (time $t_1$) when the air pressure P in the housing 2 measured by the air pressure measuring unit 50 increased to the maximum value Pmax is calculated. The amount of change $\Delta P$ in the air pressure P in this case can be calculated according to $$\Delta P = P\text{max} - Pt \tag{2}$$

where Pt represents the air pressure P in the housing 2 measured after the predetermined time $\Delta t$ has passed since time $t_1$.

The calculated amount of change $\Delta P$ in the air pressure P in the housing 2 is then compared with an amount of change $\Delta Pn$ (see FIG. 7B) in the air pressure P calculated by conducting the same experiment (or theoretically calculated) in the radiological imaging apparatus 1 in the brand-new state (or a state where the waterproof performance is normal). If there is no significant difference between the two amounts of change $\Delta P$ and $\Delta Pn$, the waterproof performance of the radiological imaging apparatus 1 is determined to be normal. If there is a significant difference between the two amounts of change ΔP and ΔPn, the waterproof performance of the radiological imaging apparatus 1 can be determined not to be normal, or the waterproof performance can be determined to have deteriorated.

Alternatively, a check can be made to determine to what degree the waterproof performance of the radiological imaging apparatus 1 has deteriorated, or determine the degree of deterioration, based on the size of the difference between the two amounts of change ΔP and ΔPn.

[Notification of a Determination Result]

A user or maintenance personnel can be notified of a result of determination (as to whether or not the waterproof performance is normal, or a degree of deterioration) carried out on the waterproof performance of the radiological imaging apparatus 1 in the above described manner. In this step, the indicators 40 of the radiological imaging apparatus 1 is made to display a predetermined color, the number of the indicators 40 to be turned on is adjusted, the indicators 40 are made to blink in a certain manner, or the result of the determination is displayed on the screen provided on the radiological imaging apparatus 1 or is output as a sound (notification step).

Alternatively, information about a result of the determination may be transferred from the radiological imaging apparatus 1 to an external computer such as a console, a service station, or the like, and the result is displayed on the display screen of the computer or the like or is output as a sound, for example, so that a user or maintenance personnel can be notified of the result of the determination (notification step). With this structure, the user or maintenance personnel who has received the notification can appropriately correct the degraded waterproof performance by repairing the radiological imaging apparatus 1, replacing components, or the like.

[Effects]

As described above, the method of testing waterproof performance of a radiological imaging apparatus according to this embodiment includes: the load application step (step S1 in FIG. 5B) of continuing to apply a load to the housing 2 of the radiological imaging apparatus 1; the air pressure measurement step (step S2) of measuring the air pressure P in the housing 2 with the air pressure measuring unit 50, the air pressure P changing while the load application to the housing 2 of the radiological imaging apparatus 1 continues; and the waterproof performance determination step (step S3) of determining whether the waterproof performance of the radiological imaging apparatus 1 is normal based on the change rate $dP/dt$ or the like of the measured air pressure P in the housing 2, or the time T that has passed before the air pressure P in the housing 2 drops to the predetermined air pressure P.

Therefore, there is no need to prepare a testing device equipped with a chamber or the like that can change the inner air pressure, or take the radiological imaging apparatus 1 to a place where such a testing device exists, as in the waterproof performance testing method disclosed in JP 2009-121965 A. Instead, the housing 2 of the radiological imaging apparatus 1 simply needs to be pressed with a hand, or a weight needs to be placed on the housing 2. Accordingly, the waterproof performance of the radiological imaging apparatus 1 can be readily tested.

Further, there is no need to change the temperature in the housing 2 of the radiological imaging apparatus 1 as in the waterproof performance testing method disclosed in JP 2010-151656 A. Accordingly, there is no need to wait until the temperature stabilizes, and the air pressure P in the housing 2 is measured simply after the housing 2 of the radiological imaging apparatus 1 is pressed with a hand or a weight is placed on the housing 2. Thus, only a short period of time is required to test the waterproof performance of the radiological imaging apparatus 1.

Furthermore, the air pressure sensor to be used as the air pressure measuring unit 50 does not need to be highly-sophisticated or expensive, but may be an inexpensive one. Accordingly, it is possible to test the waterproof performance of the radiological imaging apparatus 1 at low costs.

Second Embodiment

In the above described first embodiment, the load application step (step S1 in FIG. 5B) and the air pressure measurement step (step S2) are carried out while the vent hole H (see FIG. 4) is left open. However, these steps can be carried out, with the vent hole H being closed.

Figure 8:
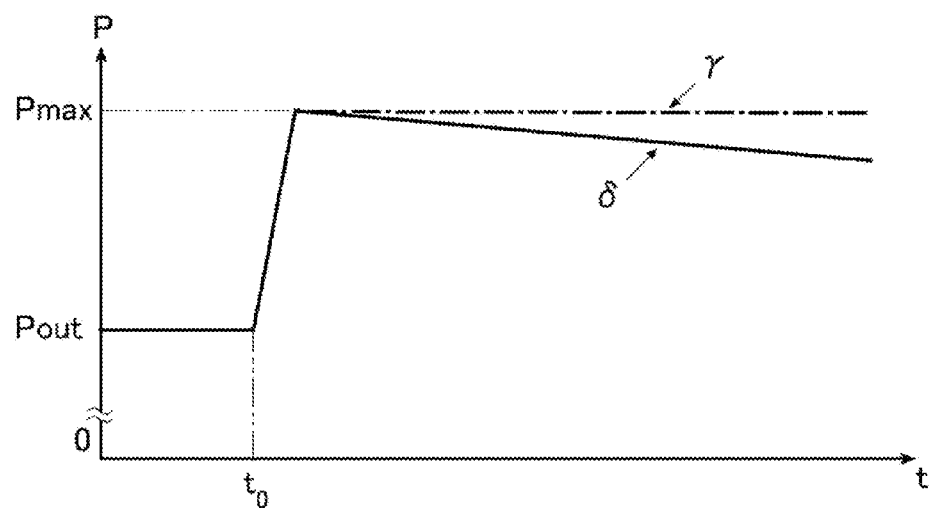
FIG. 8 is a graph showing an example of the time-series data of the air pressure in a state where the waterproof performance measured when the vent hole is closed has deteriorated, and an example of the time-series data in a state where the waterproof performance has not deteriorated.

In this case, when the housing 2 of the radiological imaging apparatus 1 is pressed with a hand or a weight is placed on the housing 2 to apply a load to the housing 2, the air in the housing 2 does not flow out as long as the waterproof performance is normal. If the load application is continued, the air pressure P in the housing 2 shoots up when the load application to the housing 2 is started (time $t_0$) and increases to the maximum value Pmax of the air pressure P (time $t_1$), as shown in FIGS. 6A and 6B, and FIGS. 7A and 7B. After that, however, the air pressure P in the housing 2 is maintained almost constant as indicated by a dot-and-dash line γ in FIG. 8.

In a case where the waterproof performance has deteriorated, and the shields and packings are damaged as described above, when a load is applied to the housing 2 of the radiological imaging apparatus 1 while the vent hole H is closed as described above, the air in the housing 2 flows out through the damaged portions and the like. As a result, after the air pressure P in the housing 2 increases to the maximum value Pmax of the air pressure P (time $t_1$), the air pressure P in the housing 2 gradually decreases as indicated by a solid line 5 in FIG. 8.

Therefore, in the waterproof performance determination step (step S3 in FIG. 5B) in this case, a check can also be made to determine whether the waterproof performance of the radiological imaging apparatus 1 is normal and determine a degree of deterioration according to any of the above described first to third determination techniques based on the change rate of the air pressure P in the housing 2 measured by the air pressure measuring unit 50 (the first determination technique), the time T that has passed before the air pressure P inside the housing 2 drops to the predetermined air pressure P* (the second determination technique), or the amount of change ΔP in the air pressure P in the housing 2 that has dropped in the predetermined time Δt (the third determination technique).

This structure according to the second embodiment can achieve the same excellent effects as those of the method of testing waterproof performance of a radiological imaging apparatus according to the above described first embodiment.

It should be noted that there are cases where the radiological imaging apparatus 1 in the brand-new state is designed to allow the air to flow out of the housing 2 through a portion other than the vent hole H (such as the portion in which the power switch 37 (see FIG. 1) is provided). The same applies in the other embodiments. In such a case, even if the vent hole H is closed, the air pressure P in the housing 2 gradually decreases after reaching the maximum value Pmax. However, if the waterproof performance has deteriorated as the shields and packings are damaged at other portions in this case, the air pressure P in the housing 2 also drops more rapidly than in the radiological imaging apparatus 1 in the brand-new state. Accordingly, it is possible to accurately determine whether the waterproof performance of the radiological imaging apparatus 1 is normal and determine the degree of deterioration, using any of the above described first to third determination techniques.

Third Embodiment

In the above described first and second embodiments, the housing 2 of the radiological imaging apparatus 1 is pressed with a hand, or a weight is placed on the housing 2, so as to continue load application to the housing 2 in the load application step (step S1 in FIG. 5B). Although a load is applied to the housing 2 of the radiological imaging apparatus 1 to cause the air to flow out of the housing 2 through the vent hole H in the load application step in this embodiment, the load application to the housing 2 of the radiological imaging apparatus 1 may be stopped, and the air pressure P in the housing 2 that continues to increase thereafter may be measured with the air pressure measuring unit 50 in the air pressure measurement step (step S2).

In the description below, the case where a load is applied to the portion 51 shown in FIG. 5A will not be explained, but a load can also be applied to the portion 51 in this embodiment.

Figure 9:
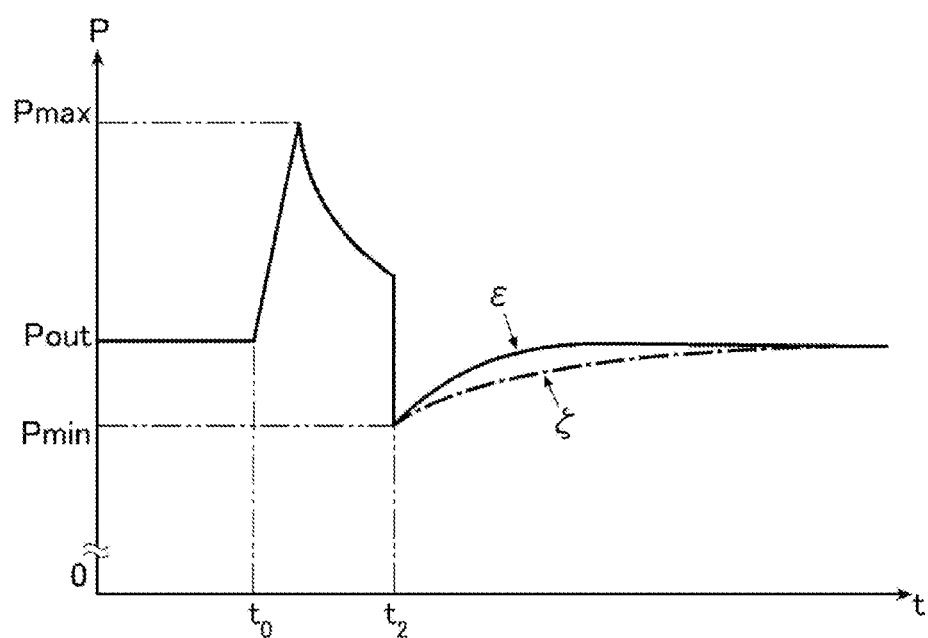
FIG. 9 is a graph showing an example of the time-series data of the air pressure in a state where the waterproof performance measured in the third embodiment has deteriorated, and an example of the time-series data in a state where the waterproof performance has not deteriorated.

In this case, when load application to the housing 2 of the radiological imaging apparatus 1 is started in the load application step (time $t_0$), the air pressure P in the housing 2 increases as shown in FIG. 9, and at the same time, the air flows out of the housing 2 through the vent hole H as in the above described first embodiment. When the load application is stopped (or the hand or the weight applying a load to the housing 2 is removed from the housing 2) at a time (time $t_2$), the deformed housing 2 tries to return to its original shape.

Although the housing 2 tries to return to its original shape, the external air does not flow into the housing 2 through the vent hole H at once, and therefore, the air pressure P in the housing 2 becomes lower than the outside atmospheric pressure Pout due to the resilience of the housing 2 trying to return to its original shape. As a result, the air pressure P in the housing 2 drops to the minimum value Pmin, which is lower than the outside atmospheric pressure Pout. That is, the air pressure P in the housing 2 at this point is so-called negative pressure.

As the external air flows into the housing 2 through the vent hole H, the air pressure P in the housing 2 gradually increases, and the deformed housing 2 gradually returns to its original shape. Eventually, the air pressure P in the housing 2 increases to the outside atmospheric pressure Pout, and the housing 2 returns to its original shape. Therefore, the air pressure P in the housing 2 fluctuates over time as shown in FIG. 9.

At this point, the waterproof performance of the radiological imaging apparatus 1 has deteriorated. If the shields or packings are damaged as described above, the air flows into the housing 2 in the negative-pressure state through portions other than the vent hole H. As a result, the air pressure P in the housing 2 relatively rapidly increases to the outside atmospheric pressure Pout, as indicated by a solid line $\epsilon$ in the graph in FIG. 9.

In a case where the radiological imaging apparatus 1 is in the brand-new state without any waterproof performance deterioration, on the other hand, the external air flows into the housing 2 in a negative-pressure state only through the vent hole H, the inflow velocity of the air becomes lower than that in a case where the waterproof performance of the radiological imaging apparatus 1 has already deteriorated. Therefore, as indicated by a dot-and-dash line $\xi$ in the graph in FIG. 9, the air pressure P in the housing 2 slowly increases to the outside atmospheric pressure Pout.

In view of this, in the waterproof performance determination step (step S3 in FIG. 5B) in the third embodiment, it is also possible to determine whether the waterproof performance of the radiological imaging apparatus 1 is normal and determine the degree of deterioration based on the above described change rate of the air pressure P, the time T, the amount of change $\Delta P$ in the air pressure P, or the like, according to the above described first to third determination techniques.

However, the third embodiment differs from the above described first and second embodiments in that, after a load is applied to the housing 2 of the radiological imaging apparatus 1 to release the air in the housing 2 to the outside through the vent hole H, and the load application is stopped, the above described determination is conducted based on the change rate of the air pressure P or the like at a time when the air pressure P in the housing 2 increases from the minimum value Pmin, which is lower than the outside atmospheric pressure Pout.

Therefore, in the waterproof performance determination step (step S3 in FIG. 5B) in the method of testing waterproof performance of a radiological imaging apparatus according to the third embodiment, the above described determination is conducted based on the change rate of the air pressure P in the housing 2 measured by the air pressure measuring unit 50 (the first determination technique), the time T that has passed before the air pressure P in the housing 2 increases to a predetermined air pressure (the second determination technique), or the amount of change $\Delta P$ in the air pressure P in the housing 2 that has increased in a predetermined time $\Delta t$ (the third determination technique).

As in the first and second embodiments, the change rate at this point in the above described first determination technique may be the time derivative dP/dt of the air pressure P in the housing 2 (or $\Delta P/\Delta t$ calculated from a predetermined time interval $\Delta t$ and the amount of change $\Delta P$ in the air pressure P during the time interval $\Delta t$; the same applies in the cases described below). However, in a case where the time derivative dP/dt depends on the difference Pout-Pmin between the outside atmospheric pressure Pout and the minimum value Pmin of the air pressure P in the housing 2, it is possible to use a time derivative dP/dt/(Pout-Pmin) per unit air pressure, which is obtained by dividing dP/dt by Pout-Pmin.

Further, the predetermined air pressure in the above described second determination technique can be set as an air pressure lower than the outside atmospheric pressure Pout by 10 of the difference Pout-Pmin between the outside atmospheric pressure Pout and the minimum value Pmin, for example. In this case, measurement of the time T is started when the air pressure P in the housing 2 temporarily drops to the minimum value Pmin (see time $t_2$ in FIG. 9), and the time T that passes before the air pressure P in the housing 2 increases to the above mentioned air pressure is determined. That is, the time T that has passed since the air pressure P in the housing 2 dropped to the minimum value Pmin till the air pressure P increases to an air pressure P that is lower than the outside atmospheric pressure Pout by (Pout−Pmin)×0.1 is calculated according to $$P^{}=P\text{out}-(P\text{out}-P\text{min})\times 0.1 \qquad (3)$$

In this case, the predetermined air pressure P** is not limited to the above, either, and may be set at an appropriate value.

In the third embodiment, at the time of the shipment from the factory, the load to be applied to the radiological imaging apparatus 1 in the brand-new state without any waterproof performance deterioration is varied, and the temporal change in the air pressure P in the housing 2 is measured for each load (see in FIG. 9). The necessary information such as the change rate (the first determination technique), the time Tn (the second determination technique), or the amount of change ΔPn (the third determination technique) corresponding to the difference Pout-Pmin between the outside atmospheric pressure Pout at the time and the minimum value Pmin of the air pressure P in the housing 2 measured by the air pressure measuring unit 50 is calculated in advance, and the information is stored into the memory of the control unit of the radiological imaging apparatus 1 or is written into a program, for example.

As described above, the method of testing waterproof performance of a radiological imaging apparatus according to the third embodiment can also achieve the same excellent effects as those of the method of testing waterproof performance of a radiological imaging apparatus according to the above described first embodiment.

In the first and second embodiments described above, when a user or maintenance personnel presses the housing 2 of the radiological imaging apparatus 1 with a hand to apply a load to the housing 2, for example, the pressing force of the hand is not necessarily constant, and might slightly vary with time. In the third embodiment, a user or maintenance personnel also applies a load to the housing 2 by pressing the housing 2 with a hand or putting a weight on the housing 2, to release the air from the housing 2 of the radiological imaging apparatus 1. However, after the load application is stopped, negative pressure is generated due to the resilience of the deformed the housing 2 and portion 51 (see FIG. 5A), and the air flows into the housing 2, resulting in an increase in the air pressure P in the housing 2.

Since the resilience of the deformed housing 2 and portion 51 (see FIG. 5A) does not vary with time but is constant, the change rate (the first determination technique), the times T and Tn (the second determination technique), and the amounts of change ΔP and ΔPn (the third determination technique) can be accurately measured or calculated. Accordingly, the accuracy of the method of testing waterproof performance of a radiological imaging apparatus can be maintained or increased.

Fourth Embodiment

In the first to third embodiments described above, a check is made to determine whether the waterproof performance of the radiological imaging apparatus 1 is normal based on change in the air pressure P in the housing 2. Instead, sound may be generated in the housing 2 of the radiological imaging apparatus 1, and a check may be made to determine whether the waterproof performance of the radiological imaging apparatus 1 is normal based on the audio data that is output through a microphone, for example.

Figure 10A:
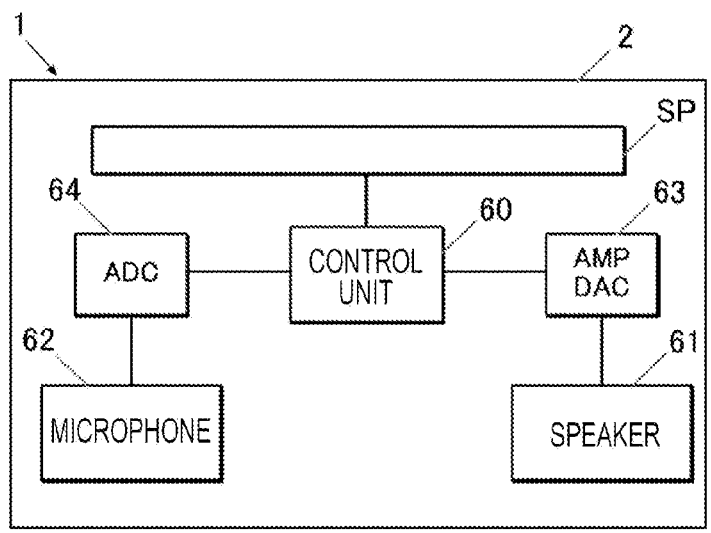
FIG. 10A is a diagram showing the structure of a radiological imaging apparatus according to a fourth embodiment.
Figure 10B:
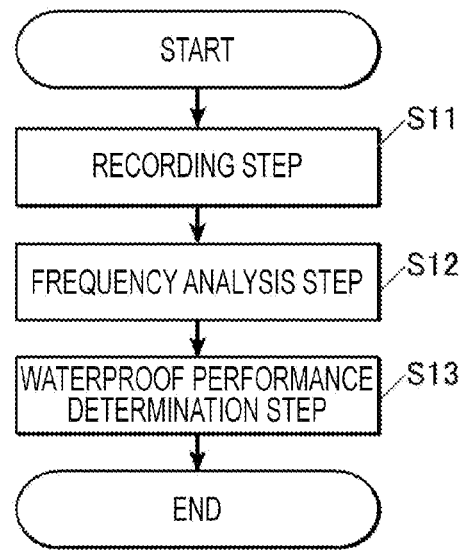
FIG. 10B is a flowchart showing the respective steps in a method of testing waterproof performance of a radiological imaging apparatus according to the fourth embodiment.

FIG. 10A is a block diagram for explaining the structure related to implementation of a method of testing the waterproof function in a radiological imaging apparatus according to a fourth embodiment. FIG. 10B is a flowchart showing the respective steps in the method of testing waterproof performance of a radiological imaging apparatus according to the fourth embodiment.

As shown in FIG. 10A, the radiological imaging apparatus 1 according to this embodiment basically has the same structure as that of each of the above described embodiments, and includes a sensor panel SP (shown in FIG. 2), a control unit 60 formed with a CPU, an FPGA, or the like (not shown), and the like in the housing 2. In this embodiment, the control unit 60 functions as the analyzing unit and the determining unit of the radiological imaging apparatus 1. However, the analyzing unit and the determining unit may be provided as devices or circuits independent of the control unit 60.

In this embodiment described below, the control unit 60 of the radiological imaging apparatus 1 also carries out a waterproof performance testing process on the radiological imaging apparatus 1. However, necessary information such as audio data may be transferred from the radiological imaging apparatus 1 to an external computer such as a console, and the external computer may carry out a waterproof performance testing process on the radiological imaging apparatus 1.

As shown in FIG. 10A, in this embodiment, a speaker 61 that emits sound, and a microphone 62 that converts the sound into audio data and records the audio data are provided in the housing 2. The speaker 61 is connected to the control unit 60 via an amplifier circuit (AMP) or a DA converter (DAC) 63 or the like, and can emit sound in accordance with an instruction from the control unit 60. The microphone 62 is connected to the control unit 60 via an AD converter (ADC) 64 or the like, and transmits recorded audio data to the control unit 60.

The control unit 60 serving as the analyzing unit (hereinafter referred to as the analyzing unit 60) is designed to conduct frequency analysis of audio data created with the microphone 62 that converts sound emitted from the speaker 61 in the housing 2 and records the audio data. The control unit 60 serving as the determining unit (hereinafter referred to as the determining unit 60) is designed to determine whether the waterproof performance of the radiological imaging apparatus 1 is normal based on the intensity distribution of the audio data subjected to the frequency analysis with respect to frequency. Referring to the flowchart shown in FIG. 10B, this aspect will be described below in detail.

As shown in the flowchart in FIG. 10B, a method of testing waterproof performance of a radiological imaging apparatus according to this embodiment basically includes the three steps: a recording step (step S11), a frequency analysis step (step S12), and a waterproof performance determination step (step S13).

In the recording step (step S11), sound is emitted from the speaker 61 in the housing 2 in accordance with an instruction of the control unit 60, and the emitted sound is converted into audio data and is recorded with the microphone 62.

When sound emitted from the speaker 61 directly reaches the microphone 62, the sound that directly reaches the microphone 62 from the speaker 61 becomes dominant over the sound that is emitted from the speaker 61, is reflected by the housing 2, the sensor panel SP, the electronic components 32, the battery 36, and the like (see FIG. 2), and then reach the microphone 62. Therefore, changes in sound that are caused by damage in the shields and packings in the housing 2 or damage in the housing 2, and affect determination of the waterproof performance of the radiological imaging apparatus 1 are not easily reflected by the audio data recorded with the microphone 62.

Although not shown in the drawing, the speaker 61 and the microphone 62 are preferably arranged as far away as possible from each other, such as being placed at diagonally opposite corners of the housing 2 substantially having a rectangular shape, for example. Alternatively, a barrier is preferably provided between the speaker 61 and the microphone 62 so that sound emitted from the speaker 61 will not directly reach the microphone 62, for example.

Figure 11A:
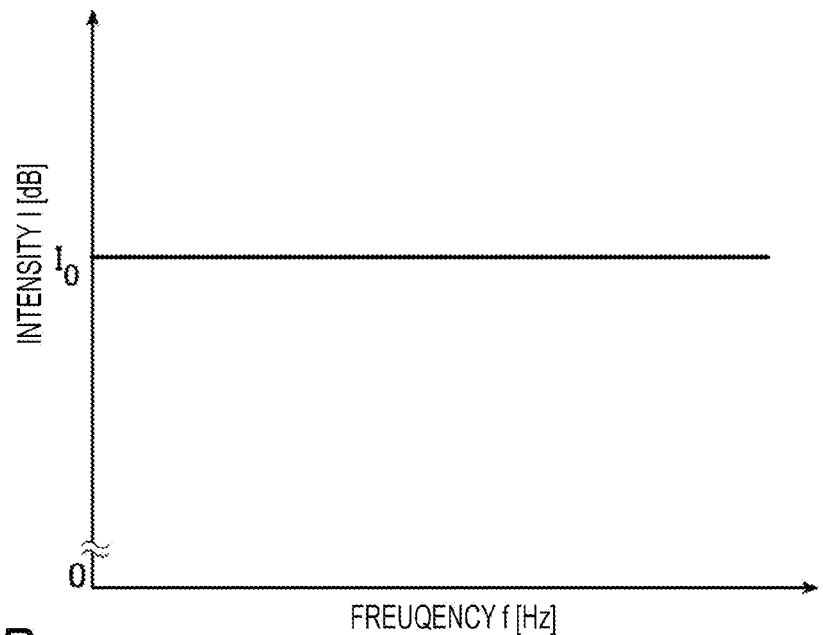
FIG. 11A is a graph showing the distribution of the intensity of white noise at respective frequencies.

The sound to be emitted from the speaker 61 is not so-called pure sound formed with a single frequency component, but is sound having frequency components or sequential frequency components. As shown in FIG. 11A, so-called white noise that has the same intensity $I_0$ at any frequency f in a case where a power spectrum is calculated through frequency analysis using Fourier transform or the like is preferably emitted from the speaker 61.

Although not shown in the drawings, the speaker 61 can be made to emit frequency sweep sound that continuously varies from a low frequency to a high frequency (or continuously varies from a high frequency to a low frequency). In the example case described below, the speaker 61 is made to emit white noise. However, the explanation below also applies in a case where the speaker 61 is made to emit frequency sweep sound.

Figure 11B:
FIG. 11B is a graph showing an example of the distribution of the intensity of audio data generated by causing a speaker in the housing to emit white noise and recording the white noise with a microphone.

When white noise is emitted from the speaker 61, and the white noise is converted into audio data and is recorded with the microphone 62, the intensity I becomes higher at the frequency f at which resonance occurs in the housing 2 or between components in the housing 2. Therefore, frequency analysis of the recorded audio data is conducted, and a power spectrum is calculated. The obtained power spectrum is a distribution in which the same intensity at any frequency f is not achieved as with white noise, but the intensity I varies depending on each frequency f, as shown in FIG. 11B.

In the housing 2 or between components in the housing 2 at this point, resonance having both ends as so-called fixed ends might be caused. In the housing 2 or between a component and the vent hole H, resonance having one end as a fixed end and the other end as a free end might be caused. However, the structure of the housing 2 or the inside of the housing 2 is complicated, and it is difficult to determine which peaks of the power spectrum shown in FIG. 11B actually correspond to which resonance. However, the power spectrum to be obtained does not change over time, unless the resonant condition changes due to damage in the shields and packings or damage in the housing 2, for example.

It is not possible to determine at which frequency f resonance is to occur, unless the speaker 61 is actually made to emit sound, and the sound data recorded with the microphone 62 is subjected to frequency analysis. The frequency f at which resonance is to occur can vary depending on the structure in the housing 2 of each radiological imaging apparatus 1. In view of this, where the speaker 61 is designed to emit white noise as described above, a frequency component that causes resonance is invariably included in white noise, regardless of the internal structure of the housing 2 of each radiological imaging apparatus 1. Accordingly, the power spectrum having a unique intensity distribution as shown in FIG. 11B can be accurately obtained.

In the frequency analysis step (step S12 in FIG. 10B), the audio data recorded with the microphone 62 is subjected to frequency analysis. This aspect has been described above. That is, the analyzing unit 60 conducts frequency analysis or perform Fourier transform or the like on the audio data that has been converted from sound emitted from the speaker 61 in the housing 2 and has been recorded with the microphone 62. As a result, the power spectrum shown in FIG. 11B is obtained, for example.

In the waterproof performance determination step (step S13), a check is made to determine whether the waterproof performance of the radiological imaging apparatus 1 is normal based on the power spectrum obtained in the above manner or on the distribution of the intensity I of the audio data subjected to the frequency analysis with respect to the frequency f (see FIG. 11B, for example).

In this embodiment, at the time of the shipment from the factory, for example, the determining unit 60 carries out the recording step (step S11) and the frequency analysis step (step S12) in the radiological imaging apparatus 1 in the brand-new state, to obtain beforehand a power spectrum in the radiological imaging apparatus 1 in the brand-new state without any waterproof performance deterioration, or a distribution of the intensity I of audio data subjected to frequency analysis with respect to the frequency f. The intensity I obtained in this situation will be hereinafter referred to as the intensity In.

The distribution of the intensity I obtained by carrying out the recording step (step S11) and the frequency analysis step (step S12) involving frequency analysis in the current radiological imaging apparatus 1 is compared with the distribution of the intensity In obtained beforehand in the above described manner in the radiological imaging apparatus 1 in the brand-new state. In this manner, a check is made to determine whether the waterproof performance of the current radiological imaging apparatus 1 is normal and determine the degree of deterioration.

Figure 12:
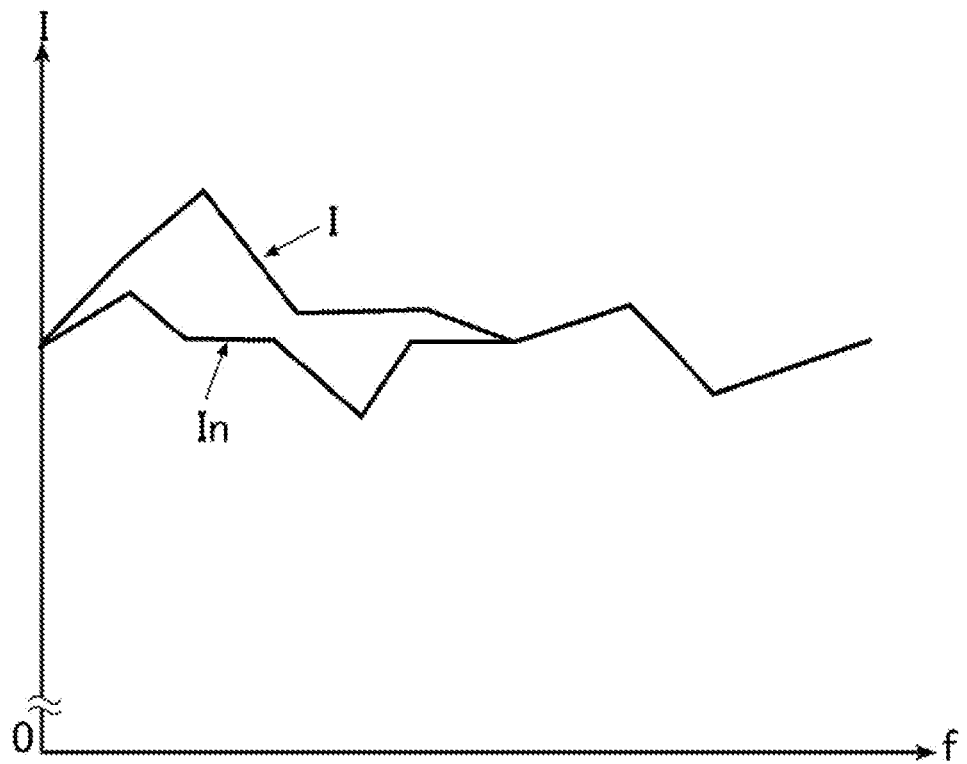
FIG. 12 is a graph for explaining that the distribution of the intensity of audio data recorded with the microphone changes as the waterproof performance of the radiological imaging apparatus deteriorates.

Specifically, where the distribution of the intensity I obtained in the current radiological imaging apparatus 1 and the distribution of the intensity In obtained beforehand in the radiological imaging apparatus 1 in the brand-new state are put into one graph, a significant difference might be observed between the intensity I and the intensity In as shown in FIG. 12, for example. Although FIG. 12 illustrates a case where the intensity I is varied so as to be higher than the intensity In, the intensity I may be varied so as to be lower than the intensity In in some other cases.

As long as the resonant condition does not change due to damage in the shields or packings or damage in the housing 2, the power spectrum to be obtained, or the distribution of the intensity I, does not change over time, as described above. Therefore, when there is a change in the distribution of the intensity I, it is safe to assume that the resonant condition has changed, or there is damage in the shields or packings or damage in the housing 2.

In view of this, in the waterproof performance determination step (step S13) according to this embodiment, the determining unit 60 compares the distribution of the intensity I obtained through the frequency analysis on the current radiological imaging apparatus 1 with the distribution of the intensity In obtained beforehand from the radiological imaging apparatus 1 in the brand-new state. If there is a frequency at which the change in the intensity I relative to the intensity In is equal to or greater than a threshold value (including cases where the intensity I becomes higher or lower than the intensity In), the waterproof performance of the radiological imaging apparatus 1 can be determined not to be normal.

Further, the degree of deterioration of the waterproof performance of the radiological imaging apparatus 1 can be determined in accordance with the amount of change in the intensity I relative to the intensity In (including cases where the intensity I becomes higher or lower than the intensity In: the same applies in cases described later), for example.

[Effects]

As described above, in the radiological imaging apparatus and the method of testing waterproof performance of the radiological imaging apparatus according to this embodiment, sound emitted from the speaker 61 in the housing 2 is converted into audio data and is recorded with the microphone 62, the recorded audio data is subjected to frequency analysis, and a check is made to determine whether the waterproof performance of the radiological imaging apparatus 1 is normal based on the distribution (power spectrum) of the intensity I of the audio data subjected to the frequency analysis with respect to the frequency f.

Therefore, there is no need to prepare a testing device or take the radiological imaging apparatus 1 to a place where such a testing device exists as in the waterproof performance testing method disclosed in JP 2009-121965 A. Instead, the speaker 61 is simply made to emit sound in the housing 2 of the radiological imaging apparatus 1 so as to implement the method of testing waterproof performance of a radiological imaging apparatus. Accordingly, the waterproof performance of the radiological imaging apparatus 1 can be readily tested.

Further, there is no need to wait until the temperature in the housing 2 of the radiological imaging apparatus 1 stabilizes as in the waterproof performance testing method disclosed in JP 2010-151656 A. Instead, the speaker 61 is simply made to emit sound in the housing 2 of the radiological imaging apparatus 1 so as to implement the method of testing waterproof performance of a radiological imaging apparatus. Accordingly, the waterproof performance of the radiological imaging apparatus 1 can be tested in a short period of time.

Furthermore, the speaker 61, the microphone 62, and the like do not need to be highly-sophisticated or expensive, but may be inexpensive ones. Accordingly, it is possible to test the waterproof performance of the radiological imaging apparatus 1 at low costs.

[Time to Implement a Method of Testing Waterproof Performance of a Radiological Imaging Apparatus]

The methods of testing waterproof performance of a radiological imaging apparatus according to the above described respective embodiments can be implemented at the times described below, for example.

The above described method according to the fourth embodiment using sound can be implemented at a desired time, as long as the power supply to the radiological imaging apparatus 1 is on, for example. A user such as a radiological technologist operates the power switch 37 (see FIG. 1) of the radiological imaging apparatus 1, for example, and, at the time when the initial operation of the radiological imaging apparatus 1 is finished, the respective steps (see FIG. 10B) in the method of testing waterproof performance of a radiological imaging apparatus can be carried out.

In each of the first to third embodiments, on the other hand, the respective steps (see FIG. 5B) in the method of testing waterproof performance of a radiological imaging apparatus can be carried out when a user or maintenance personnel inspects or maintains the radiological imaging apparatus 1.

The methods according to the first to third embodiments described above can be implemented at a time of imaging, for example. Specifically, in a case where the radiological imaging apparatus 1 is placed on a bed or a table, and the body of a patient as the object is placed on the radiological imaging apparatus 1 for imaging, a load is applied to the housing 2 as the body of the patient is placed on the housing 2 of the radiological imaging apparatus 1. This phenomenon can be utilized in implementing the method of testing waterproof performance of a radiological imaging apparatus.

For example, a user such as a radiological technologist can operate the selector switch 38 (see FIG. 1) of the radiological imaging apparatus 1, to instruct the radiological imaging apparatus 1 to start measuring the air pressure P in the housing 2 with the air pressure measuring unit 50 (see FIG. 5A).

Further, the air pressure measuring unit 50 can be made to constantly measure the air pressure P in the housing 2, for example. When the air pressure P being measured in the housing 2 increases to a predetermined threshold value or higher, for example, the control unit of the radiological imaging apparatus 1 or an external computer or the like can determine whether the waterproof performance of the radiological imaging apparatus 1 is normal based on the temporal change (see FIGS. 6A and 6B) in the air pressure P in the housing 2 or the pattern of change in the air pressure P in the housing 2 after the air pressure P becomes equal to or higher than the predetermined threshold value.

Further, in a case where the method of testing waterproof performance of a radiological imaging apparatus according to the third embodiment is implemented, when the air pressure P in the housing 2 temporarily becomes equal to or lower than a threshold value set at a lower value than the outside atmospheric pressure Pout after having increased as shown in FIG. 9, for example, the control unit of the radiological imaging apparatus 1 or an external computer or the like can determine whether the waterproof performance of the radiological imaging apparatus 1 is normal based on the temporal change (see FIG. 9) in the air pressure P in the housing 2 or the pattern of change in the air pressure P in the housing 2 after the air pressure P becomes equal to or lower than the predetermined threshold value.

It should be understood that the present invention is not limited to the above described embodiments, and various changes may be made to them without departing from the scope of the invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A method of testing waterproof performance of a radiological imaging apparatus,
   the radiological imaging apparatus including:
   a sensor panel including a plurality of radiation detecting elements two-dimensionally arranged;
   a housing containing the sensor panel; and
   an air pressure measuring unit configured to measure an air pressure in the housing,
   the housing having a vent hole allowing the air to flow into and out of the housing,
   the method comprising:
   a load application step of continuing to apply a load to the housing of the radiological imaging apparatus;
   an air pressure measurement step of measuring the air pressure in the housing with the air pressure measuring unit, the air pressure changing while the load is being applied to the housing of the radiological imaging apparatus; and
   a waterproof performance determination step of determining whether the waterproof performance of the radiological imaging apparatus is normal based on a pattern of change in the measured air pressure in the housing.

2. The method of testing waterproof performance of a radiological imaging apparatus according to claim 1, wherein, in the waterproof performance determination step, a check is made to determine whether the waterproof performance of the radiological imaging apparatus is normal based on one of a change rate of the measured air pressure in the housing, a time elapsing before the air pressure in the housing drops to a predetermined air pressure, and an amount of change in the air pressure dropping in a predetermined time in the housing.

3. The method of testing waterproof performance of a radiological imaging apparatus according to claim 1, wherein at least the load application step and the air pressure measurement step are carried out, with the vent hole being closed.

4. A method of testing waterproof performance of a radiological imaging apparatus,
the radiological imaging apparatus including:
a sensor panel including a plurality of radiation detecting elements two-dimensionally arranged;
a housing containing the sensor panel; and
an air pressure measuring unit configured to measure an air pressure in the housing,
the housing having a vent hole allowing the air to flow into and out of the housing,
the method comprising:
a load application step of applying a load to the housing of the radiological imaging apparatus to release the air in the housing to the outside through the vent hole;
an air pressure measurement step of measuring the air pressure in the housing with the air pressure measuring unit, the air pressure continuing to increase after the application of the load is stopped; and
a waterproof performance determination step of determining whether the waterproof performance of the radiological imaging apparatus is normal based on a pattern of change in the measured air pressure in the housing.

5. The method of testing waterproof performance of a radiological imaging apparatus according to claim 4, wherein, in the waterproof performance determination step, a check is made to determine whether the waterproof performance of the radiological imaging apparatus is normal based on one of a change rate of the measured air pressure in the housing, a time elapsing before the air pressure in the housing increases to a predetermined air pressure, and an amount of change in the air pressure increasing in a predetermined time in the housing.

6. The method of testing waterproof performance of a radiological imaging apparatus according to claim 1, wherein a ventilation filter for preventing liquid from penetrating into the housing is provided in the vent hole.

7. The method of testing waterproof performance of a radiological imaging apparatus according to claim 1, wherein, in the load application step, the load is applied to a portion of the housing of the radiological imaging apparatus, the portion being softer than the other portions of the housing.

8. The method of testing waterproof performance of a radiological imaging apparatus according to claim 1, wherein, in the waterproof performance determination step, a check is made to determine whether the waterproof performance of the radiological imaging apparatus is normal based on a comparison between a pattern of change in the measured air pressure in the housing and a pattern of change in an air pressure measured in the housing of the radiological imaging apparatus in a brand-new state.

9. A method of testing waterproof performance of a radiological imaging apparatus,
the radiological imaging apparatus including:
a sensor panel including a plurality of radiation detecting elements two-dimensionally arranged;
a housing containing the sensor panel;
a speaker configured to emit sound, the speaker being provided in the housing; and
a microphone configured to convert the sound into audio data, the microphone being provided in the housing,
the method comprising:
a recording step of converting the sound emitted from the speaker in the housing into the audio data and recording the audio data;
a frequency analysis step of subjecting the recorded audio data to frequency analysis; and
a waterproof performance determination step of determining whether the waterproof performance of the radiological imaging apparatus is normal based on a distribution of intensity of the audio data subjected to the frequency analysis with respect to frequency.

10. The method of testing waterproof performance of a radiological imaging apparatus according to claim 9, wherein, in the recording step, the speaker is made to emit one of white noise and frequency sweep sound.

11. The method of testing waterproof performance of a radiological imaging apparatus according to claim 9, wherein, in the waterproof performance determination step, a check is made to determine whether the waterproof performance of the radiological imaging apparatus is normal based on a comparison between the distribution of the intensity obtained through the frequency analysis and a distribution of the intensity obtained by carrying out the recording step and the frequency analysis step in the radiological imaging apparatus in a brand-new state.

12. The method of testing waterproof performance of a radiological imaging apparatus according to claim 1, further comprising a notification step of issuing a notification of a result of the determination after the waterproof performance determination step.

13. A radiological imaging apparatus comprising:
a sensor panel including a plurality of radiation detecting elements two-dimensionally arranged;
a housing containing the sensor panel;
a speaker configured to emit sound, the speaker being provided in the housing;
a microphone configured to convert the sound into audio data and record the audio data, the microphone being provided in the housing,
an analyzing unit configured to subject the audio data to frequency analysis, the audio data being converted from the sound emitted from the speaker in the housing and being recorded with the microphone; and
a determining unit configured to determine whether the waterproof performance of the radiological imaging apparatus is normal based on a distribution of intensity of the audio data subjected to the frequency analysis with respect to frequency.

14. The method of testing waterproof performance of a radiological imaging apparatus according to claim 4, wherein a ventilation filter for preventing liquid from penetrating into the housing is provided in the vent hole.

15. The method of testing waterproof performance of a radiological imaging apparatus according to claim 4, wherein, in the load application step, the load is applied to a portion of the housing of the radiological imaging apparatus, the portion being softer than the other portions of the housing.

16. The method of testing waterproof performance of a radiological imaging apparatus according to claim 4, wherein, in the waterproof performance determination step, a check is made to determine whether the waterproof performance of the radiological imaging apparatus is normal based on a comparison between a pattern of change in the measured air pressure in the housing and a pattern of change in an air pressure measured in the housing of the radiological imaging apparatus in a brand-new state.

17. The method of testing waterproof performance of a radiological imaging apparatus according to claim 4, further comprising a notification step of issuing a notification of a result of the determination after the waterproof performance determination step.

18. The method of testing waterproof performance of a radiological imaging apparatus according to claim 9, further comprising a notification step of issuing a notification of a result of the determination after the waterproof performance determination step.

\* \* \* \* \*